US011033203B2

United States Patent
Allsworth et al.

(10) Patent No.: US 11,033,203 B2
(45) Date of Patent: *Jun. 15, 2021

(54) SYSTEMS AND DEVICE FOR CAPTURING BREATH SAMPLES

(71) Applicant: Owlstone Medical Limited, Cambridge (GB)

(72) Inventors: Max Allsworth, Essex (GB); Duncan Apthorp, Cambridge (GB); Marc van der Schee, Amsterdam (NL); Rob Smith, Cambs (GB); Jasper Boschmans, Cambs (GB); Simon Kitchen, Cambridgeshire (GB)

(73) Assignee: Owlstone Medical Limited, Cambridge (GB)

( * ) Notice: Subject to any disclaimer, the term of this patent is extended or adjusted under 35 U.S.C. 154(b) by 367 days.

This patent is subject to a terminal disclaimer.

(21) Appl. No.: 15/429,839

(22) Filed: Feb. 10, 2017

(65) Prior Publication Data

US 2017/0303822 A1    Oct. 26, 2017

Related U.S. Application Data

(60) Provisional application No. 62/327,200, filed on Apr. 25, 2016.

(51) Int. Cl.
*A61B 5/00* (2006.01)
*A61B 5/097* (2006.01)
(Continued)

(52) U.S. Cl.
CPC .............. *A61B 5/097* (2013.01); *A61B 5/082* (2013.01); *A61B 5/743* (2013.01);
(Continued)

(58) Field of Classification Search
CPC ......... A61B 5/082; A61B 5/097; A61B 5/087; A61B 5/0836; A61B 5/742; G01N 33/497;
(Continued)

(56) References Cited

U.S. PATENT DOCUMENTS 3,661,528 A    5/1972  Falk
3,808,694 A *  5/1974  Hutchinson ............ G01G 23/37
                                                    33/512

(Continued)

FOREIGN PATENT DOCUMENTS

WO    WO2008060165    5/2008
WO    WO2013026902    2/2013
WO    WO2015031848    3/2015

OTHER PUBLICATIONS

International Search Report in PCT Application PCT/GB2017/050094, dated Apr. 5, 2017.
(Continued)

*Primary Examiner* — May A Abouelela
(74) *Attorney, Agent, or Firm* — Barnes & Thornburg LLP

(57) ABSTRACT

There is provided a device for collecting a breath portion from a patient for analysis, comprising a housing structure including an inlet port associated with a mask structure for receiving a portion of the patient's breath, at least one sensor operatively coupled to the inlet port for detecting one or more parameters regarding the patient's breath, at least one collection container for collecting a portion of the patient's breath received in the inlet port, at least one pump for pumping a selective portion of the patient's breath from the inlet port to the at least one collection container and a control system for controlling operation of the at least one sensor and at least one pump. The control system selectively (Continued)

operates the pump based on sensed parameters such as $CO_2$ and/or pressure to collect breath samples.

22 Claims, 14 Drawing Sheets

(51) Int. Cl.
*A61B 5/08* (2006.01)
*B01D 46/00* (2006.01)
*B01D 53/02* (2006.01)
*B01D 53/30* (2006.01)
*G01N 33/497* (2006.01)

(52) U.S. Cl.
CPC ......... *B01D 46/0028* (2013.01); *B01D 53/02* (2013.01); *B01D 53/30* (2013.01); *G01N 33/497* (2013.01); B01D 2253/102 (2013.01); B01D 2257/708 (2013.01); G01N 2033/4975 (2013.01)

(58) Field of Classification Search
CPC ........... G01N 33/4972; G01N 2800/12; G01N 2033/4975; G01N 21/3504; A61M 2230/432; A61M 16/085; A61M 2016/0027; A61M 2202/0225; B01D 46/0028; B01D 53/02; B01D 53/30; B01D 2253/102; B01D 2257/708
USPC ......................... 600/301, 532, 300, 531, 543
See application file for complete search history.

(56) References Cited

U.S. PATENT DOCUMENTS

| | | | | |
|---|---|---|---|---|
| 5,425,374 A | * | 6/1995 | Ueda | A61B 5/0836 422/84 |
| 5,465,728 A | * | 11/1995 | Phillips | A61B 5/097 600/543 |
| 6,067,983 A | * | 5/2000 | Stenzler | A61B 5/097 128/204.23 |
| 6,582,376 B2 | * | 6/2003 | Baghdassarian | A61B 5/0836 600/529 |
| 7,101,341 B2 | * | 9/2006 | Tsukashima | A61B 5/083 422/84 |
| 7,600,439 B1 | * | 10/2009 | Patterson | G01N 1/405 73/23.37 |
| 8,052,933 B2 | * | 11/2011 | Schirmer | G01N 1/22 422/500 |
| 8,479,731 B2 | * | 7/2013 | Heinonen | A61B 5/0836 128/200.15 |
| 9,239,323 B2 | * | 1/2016 | Keays | G01N 33/4972 |
| 9,936,897 B2 | * | 4/2018 | Carlson | A61B 5/083 |
| 10,034,621 B2 | * | 7/2018 | Wondka | A61B 5/0816 |
| 2003/0109794 A1 | * | 6/2003 | Phillips | A61B 5/097 600/543 |
| 2007/0062255 A1 | * | 3/2007 | Talton | G01N 33/497 73/23.3 |
| 2008/0038154 A1 | * | 2/2008 | Longbottom | A61B 5/083 422/84 |
| 2008/0234553 A1 | * | 9/2008 | Urman | A61B 5/0059 600/300 |
| 2009/0062686 A1 | * | 3/2009 | Hyde | A61B 5/1112 600/558 |
| 2010/0081957 A1 | * | 4/2010 | Hyde | A61M 15/02 600/532 |
| 2012/0277794 A1 | * | 11/2012 | Kountotsis | A61B 5/6802 606/234 |
| 2012/0302907 A1 | * | 11/2012 | Palmskog | A61B 5/082 600/532 |
| 2014/0094669 A1 | * | 4/2014 | Jaffe | A61M 16/0666 600/324 |
| 2014/0194703 A1 | | 7/2014 | Wondka | |
| 2014/0228699 A1 | | 8/2014 | Causevic | |
| 2014/0235961 A1 | * | 8/2014 | Brugnoli | A61B 5/087 600/301 |
| 2014/0288454 A1 | * | 9/2014 | Paz | A61B 5/4845 600/532 |
| 2014/0378790 A1 | * | 12/2014 | Cohen | A61B 5/486 600/309 |
| 2015/0005657 A1 | * | 1/2015 | Nijsen | A61B 5/097 600/532 |
| 2015/0025407 A1 | * | 1/2015 | Eichler | A62B 23/06 600/532 |
| 2015/0196251 A1 | * | 7/2015 | Outwater | A61B 5/4875 600/301 |
| 2015/0265184 A1 | | 9/2015 | Wondka | |
| 2015/0335267 A1 | | 11/2015 | Cormier | |
| 2016/0000358 A1 | * | 1/2016 | Lundin | A61B 5/097 600/532 |
| 2016/0022946 A1 | * | 1/2016 | Sislian | A61B 10/00 600/543 |
| 2016/0166177 A1 | * | 6/2016 | Smart | A61B 5/082 600/541 |
| 2016/0345910 A1 | * | 12/2016 | Ahmad | A61B 5/082 |
| 2017/0045495 A1 | * | 2/2017 | Trowell | G01N 33/5082 |
| 2017/0074857 A1 | * | 3/2017 | Dennis | A61B 5/4833 |
| 2017/0107556 A1 | * | 4/2017 | Koo | A61B 5/4836 |
| 2017/0160265 A1 | * | 6/2017 | Haick | G01N 1/2214 |
| 2017/0227455 A1 | * | 8/2017 | Kakuno | A61B 5/0836 |
| 2017/0319069 A1 | * | 11/2017 | Lepek | G01N 21/3504 |

OTHER PUBLICATIONS

Annex to Communication Relating to the Results of the Partial International Search in PCT/GB2017/051119.

* cited by examiner a) GC-MS results from two breath samples including retention time matched and NIST identification. b) GC-FAIMS Quality Control

SYSTEMS AND DEVICE FOR CAPTURING BREATH SAMPLES

FIELD OF THE INVENTION

The present invention relates generally to a medical device and protocols to facilitate diagnosis of medical conditions based on breath and body volatile biomarker analysis, and in particular, to an apparatus, system and method that collects volatile biomarkers for assessment of health and disease diagnosis, monitoring and assessment of prognosis.

BACKGROUND OF THE INVENTION

The metabolome is the aggregate of small molecules that originate from metabolic processes throughout the body. Metabolomic analysis is appealing for biomedical applications as relatively small changes in gene-expression or protein activity can have a profound effect on the concentrations of downstream metabolites. A significant fraction of these metabolites are volatile. These biomarkers are of specific interest in health and disease as they are excreted through breath, urine, feces and skin providing non-invasive access. Volatile biomarkers (VBs) consist of both volatile organic compounds (VOCs) and Volatile inorganic compounds (VICs). Examples of VBs implicated in health and disease include alkanes, alkenes, acetone, isoprene, NO, CO and aldehydes.

Any change in the function of an organism changes cellular metabolism by definition. Consequently this affects the metabolome and its volatile fraction. The resulting changes in VBs may therefore serve as biomarkers for assessment of a wide range of normal physiological and pathophysiological processes.

The rate at which VBs are exhaled is the net effect of several interacting (bio)chemical processes; intra and extra-cellular degradation, solubility of the compound in extra-cellular fluid, fat and blood, the affinity with extracellular matrix and carrier proteins, the concentration gradient between the alveolar and bronchial air, the vapor pressure and alveolar ventilation. This results in a chemical equilibrium of a given compound between breath, blood and fat which can be described by that substance's physiochemical partition constant.

To date several thousands of individual VBs have been identified generally occurring in the parts per million/parts per billion range. VBs may be of local, systemic or exogenous origins (FIG. 1).

In breath locally produced compounds diffuse directly into alveoli or the airway lumen along the respiratory tract. An example is the biological mechanism behind VOC formation in the presence of Reactive Oxygen Species (ROS). ROS are responsible for increased levels of oxidative stress associated with disease in general. ROS drive cell wall lipid peroxidation resulting in production of ethane and n-pentane. These substances show only low solubility in blood and are therefore excreted into breath within minutes of their formation in tissues. Hence, exhaled concentrations of ethane and n-pentane can be used to monitor the degree of oxidative damage in the body.

Volatiles of systemic origins are derived from the circulation after originating from metabolic processes elsewhere and dissolving into the blood. Therefore, even non-pulmonary diseases contribute to exhaled VBs, which has successfully been used in the assessment of non-pulmonary malignancies. A well known group of systemically originating VOCs are ketone bodies like acetone, acetoacetate and hydroxybutyrate which are oxidized via the Krebs cycle in peripheral tissue as part of glucose metabolism.

Exogenous VBs can be inhaled or absorbed through the skin. They primarily originate from non-human sources and exist in three categories. Firstly, VBs that are in- and expired without any interaction with the body. A second group of exogenous VBs does interact with human tissue and can be stored inside the body for extensive periods of time[3]. The latter volatiles can therefore serve as potential biomarkers for environmental exposures and buildup of toxins such as the cigarette smoke carcinogen N-Nitrosomine. The third group of exogenous VBs is of (resident) microbial origin (predominantly bacteria, but also fungi and viruses), making them of specific interest when identifying infectious diseases or diseases linked to changes in microbiome. Since exhaled VBs reflect this broad range of (patho)physiological processes they have potential usage in 1. assessment of normal metabolic processes 2. evaluation of environmental exposure 2. therapy stratification 3. monitoring of therapy response 4. monitoring of disease activity and exacerbation prediction 5. Identification and characterisation of micro-organisms in a host. 6. Assessment of host response to micro-organisms 7. Screening for pre-morbid conditions 8. Early detection of disease in asymptomatic subjects. These potential applications are relevant in pulmonary and non-pulmonary diseases.

However, though analysis of body fluids (blood, sputum, urine) for disease diagnoses and monitoring is routine clinical practice, human breath analysis methodologies that exploit the non-invasive nature of such diagnoses are still under-developed and have not been adopted in clinical practice. Reasons underlying this lack of adoption include:

1. Reproducibility of technology: Most techniques used to date show inadequate inter and intra device reproducibility to allow deployment.

2. Technology sensitivity: VBs, especially VOCs typically occur in the ppb ppt range, many analytical systems do not have this sensitivity.

3. Selectivity of technology: As the composition of VBs is complex a system needs to be selective in detection of target compounds.

4. Unreliable sample collection: Sample collect is generally poorly standardised and validated.

5. Technology costs: Costs of classical chemical analytical instruments are prohibitive for deployment of a VB based test.

SUMMARY OF THE INVENTION

In accordance with the present invention, there is provided a device for collecting a breath portion from a patient for analysis having the preferred features as set out in the claims.

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings.

To achieve these and other advantages and in accordance with the purpose of the illustrated embodiments, in one aspect, a portable microprocessor-controlled breath collection apparatus collects pre-specified fractions of in- or expired air (e.g., alveolar) VBs into sorbent tubes which are then analyzed by chemical analytical techniques such as Gas Chromatography and Mass Spectrometry and Ion-Mobility Spectrometry (IMS) techniques, and in particular, Field Asymmetric Ion Mobility Spectrometry (FAIMS) techniques for disease diagnosis.

Described is an apparatus, system and method which collects and analyses biomarkers for the assessment of physiological and pathophysiological processes in health and disease (e.g. infectious, inflammatory and neoplastic disease) in an organism, including a human (hereinafter collectively referred to as a "patient"). In one or more illustrated embodiments, a measured quantity of breath (or other source of VBs) from a patient is collected, which is subsequently analyzed to detect the presence of VBs markers for assessment of metabolism in health and disease.

Therefore, it is to be appreciated that an object of the present invention is to collect one or more samples of the VB's (including VOCs and VICs) in a patient's breath for subsequent in-vitro analysis. A purpose for collecting the VOC samples is to facilitate the diagnosis, monitoring and prognosis prediction of inflammatory, infectious and neoplastic diseases, such as lung cancer.

Accordingly, a highly accurate medical device is provided that is economical, easy to operate, portable and collects breath VBs in a reproducible manner for subsequent use of these biomarkers in a screening or diagnostic test with a high degree of accuracy. The present invention provides a device and method for diagnostic analysis of exhaled VBs and those emitted from tissue and or biological samples for reliable, low cost and non-invasive health care use.

The device may be provided with:
GC-FAIMS heated zone to minimize condensing at end of column
Splits and purge for breath samples to deal with moisture
Set up of cold trap above freezing to deal with moisture
Selection of the Tenax/Carbotrap sorbent to cover the range of chemicals that we expect to find in breath while ensuring that both sorbents are hydrophobic so that the repel the high level of water vapour found in breath.
Rationale for collecting multiple breath fractions
Potential to collect inspired air for exposure assessment
Potential to collect inspired air for correction against environmental VBs
Potential to collect volatile biomarkers originating from micro-organisms
Potential to use air supply to load inhaled air with components to perform wash-out and/or exposure experiments.
Selective Breath Capture Features
Use of a pressure sensor and $CO_2$ sensor in the device to track the patient's breathing pattern.
Use these algorithms to be able to select breath from a particular portion of the air from the respiratory system—examples of this include total breath, total breath but without mouth air, just air from the upper airway, just breath from the lower airway, combined breath from the upper and lower airways, air from the oropharynx and nasopharynx as well as air coming from the stomach. Sampling air from one part of the lung is important to localise the breath from the area of the lung that is generating the VOCs.
Sampling different parts of the breath in order to provide a control which can be used to eliminate exogenous peaks
Sampling parts of the breath which exclude the volume from the mouth in order to reduce exogenous peaks
Using pumps based on high frequency piezo technology which can be switched on and off fast enough to sample a part of breath
Using fixed flow resistance apertures to reduce the effect of variation in sampling tube resistance
Sampling the inhaled air in order to correct for exogenous compounds
Create a detailed log file of all the data collected during the breath collection for later analysis to check that the breath collection was valid.
Use two separate sampling channels so that different portions of the same patient's breath can be compared and the differences between the two samples and their similarities can be used in disease diagnosis.
Have the ability to run zero, one or two sorbent tubes on each pump so that a wide range of use cases can be covered. This includes the ability to analyse the samples from each sample type on both MS-FAIMS and GC-MS.
Calculating Thresholds
Monitoring pressure to calculate the point in a breath that originates in a particular part of the lung in order to trigger a pump activation
Using the first or second differential of the pressure to calculate the point in a breath that originates in a particular part of the lung in order to trigger a pump activation
Scaling the pressure or differential pressure thresholds according the breathing pattern of a particular patient
Using a user definable offsets on the learned thresholds to enable a small amount of overlap in sections of breath to be applied
Scaling any user definable offsets with the magnitude of the breathing so they behave the same across different patients
Using a number of previous breaths to actively change the calculated points over time to account for changes in the patients breathing over time
Applying filters or trimming outliers to learnt breath data in order to exclude anomalous breathing patterns (talking, coughing or sudden intakes of breaths) before using the pressure or first differential of the pressure to calculate the thresholds
Applying a running window of a fixed number of the most recent breaths to account for long term trends when sampling (patient relaxing and getting used to the sampling)
Using hard limits on the time an individual breath is sampled for and the pressure difference across a breath to minimise the effect of an anomalous breathing pattern
Using $CO_2$ to calculate the point in a breath that originates in a particular part of the lung in order to trigger a pump activation
Using the point of maximum $CO_2$ to identify a particular part of the lung in order to trigger a pump activation
Using the pressure at the point of maximum $CO_2$ as the trigger for a pump activation
If the $CO_2$ is lagging the breath due to its response time calculating the lag and using to find the correct pressure at the point of maximum $CO_2$
If the $CO_2$ is lagging the breath due to its response time using the end of the breath to calculate the lag and using this to find the correct pressure at the point of maximum $CO_2$ Monitoring the patients breathing rate and providing feedback to the user of the software in order to optimise the breath collection Monitoring the pressure in the mask in order to detect a poorly fit mask and providing feedback to the user of the software if detected Compare the pressure drop inside the system to generate a particular flow rate to expected pump behaviour over time in order to detect a system leak or pump failure Patient Safety Monitoring The $CO_2$ sensor can be used to monitor the adequacy of the patients breathing and set appropriate thresholds to abort sampling procedure in the case of hyper or hypocapnia.

The pressure sensor can be used to monitor breathing frequency and set appropriate thresholds to abort sampling in the case of hypo or hyperventilation.

The air supply of the apparatus can be used to provide the patient with additional oxygen during sampling if medically indicated.

FAIMS Sensor Technology for Detecting VOCs

Using a cold trap that uses the same sorbents as the sampling tubes to ensure that it accurately captures the VOCs found in the tube.

Holding the cold trap at a temperature above freezing so that water does not freeze on the cold trap.

Splitting the sample to only pass some of it through the analytical instrument to reduce the impact of water damage and to avoid overloading the instrument.

Load internal standards onto the sorbent tubes or onto the cold trap to enable internal QC check on the analytical measurement.

Use of a non-polar GC column to reduce interaction with water in the stationary phase and to provide a more robust method when running high volumes of samples.

Correction of retention times through the GC column by regularly testing known QC mixtures on sorbent tubes between running the breath samples and then measuring the time taken for these QC compounds to pass through the GC column and using this to correct the data from later breath samples.

Because a FAIMS system such as manufactured by Owlstone Inc. can scan very quickly then continuously scan multiple DF values while the breath sample is passing through the GC column to improve the resolution of the analytes. Use the additional separation available from the FAIMS system to separate VOCs that take the same time to pass through the GC column.

Running FAIMS at high temperature to prevent water and other compounds condensing at the FAIMS entrance. This improves the quality of the resulting spectra and prevents damage to the GC column.

Run breath samples on both the GC-FAIMS and the GC-MS and combine the data from both platforms to generate the cancer classifier. This is powerful because there are some VOCs where the GC-FAIMS is better at detecting them and some where the GC-MS is better.

Check the system by running a homologous series of compounds through to check both the GC retention times and the FAIMS performance. This is particularly important as the FAIMS can operate at a wide range of temperatures.

Complete in Place Solutions

Drawing a section of breath onto a cold trap in order to concentrate the sample before measurement on a DMS system Drawing different sections of breath onto a number of cold traps in order to concentrate the sample before measurement on a DMS system in sequence As well as samples of breath drawing in ambient air onto a trap in order to eliminate exogenous compounds Using a micro GC or short air compatible GC on a DMS system to provide basic pre-separation Running at low temperature isothermal GC conditions to prevent degradation of breath compounds Using a metal-organic framework as a sorbent to allow air to be used as the carrier gas Re-collecting sample and repeating with different thermal desorption profile or GC temperature to provide additional separation Running recollected samples only if certain peak/feature/pattern is observed—optimise for fast negative (all clear) method Combining with a NDIR/FTIR measurement to provide additional chemical information Sampling directly onto a DMS system and using Acetone or other high intensity compound as the marker of the section of breath. Using the DMS as the selector for the part of breath and loading a cold trap or sorbent tube. When collect is complete desorb the pre-concentrated sample back into the DMS

BRIEF DESCRIPTION OF THE DRAWINGS

The accompanying appendices and/or drawings illustrate various non-limiting, example, inventive aspects in accordance with the present disclosure:

FIG. 12 illustrates

DETAILED DESCRIPTION OF CERTAIN EMBODIMENTS

Figure 1:
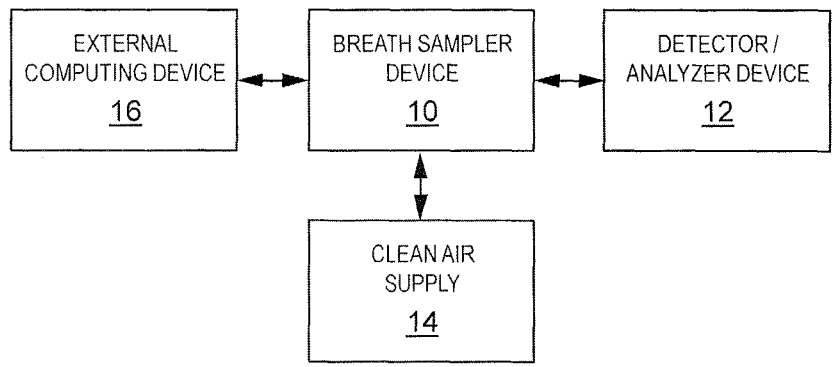
FIG. 1 illustrates a system level overview of an embodiment of the present invention.

The illustrated embodiments are now described more fully with reference to the accompanying drawings wherein like reference numerals identify similar structural/functional features. The illustrated embodiments are not limited in any way to what is illustrated as the illustrated embodiments described below are merely exemplary, which can be embodied in various forms, as appreciated by one skilled in the art. Therefore, it is to be understood that any structural and functional details disclosed herein are not to be interpreted as limiting, but merely as a basis for the claims and as a representation for teaching one skilled in the art to variously employ the discussed embodiments. Furthermore, the terms and phrases used herein are not intended to be limiting but rather to provide an understandable description of the illustrated embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the illustrated embodiments, exemplary methods and materials are now described.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the illustrated embodiments discussed below are preferably a software algorithm, program or code residing on computer useable medium having control logic for enabling execution on a machine having a computer processor. The machine typically includes memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine or run in the cloud. The embodiments described herein include such software to implement the equations, relationships and algorithms described above. One skilled in the art will appreciate further features and advantages of the illustrated embodiments based on the above-described embodiments. Accordingly, the illustrated embodiments are not to be limited by what has been particularly shown and described, except as indicated by the appended claims.

Breath VBs analysis is a non-invasive procedure. Breath tests are potentially more sensitive than blood tests because the quantity of collected analysis is limited only by the capacity of the breath collection apparatus and the patience of the donor. As such breath VB analysis allows analysis of the metabolic fraction of a large fraction of blood.

What is described below, and in accordance with one or more illustrative embodiments, is a breath sampler device (e.g. device 10 shown in the below described figures) configured and functional to capture a plurality (e.g., four (4)) samples of the Volatile Biomarkers (VBs) in a patient's in or expired air for later in vitro analysis in a separate laboratory environment (e.g., device 12 shown in the below described figures). The present invention breath sampler is designed and functional not to cause an unacceptable hazard to the patient or to the clinical staff using it. The electronics and/or software utilized in the sampler device 10 also does not interfere with the patient's vital bodily functions (e.g. breathing). Firstly the sampling mask does not impose any increased breathing resistance. The incorporated pressure and $CO_2$ sensor allow tracing of breathing frequency and efficacy. The operator and/or end-user can program an alarm to sound if hyper/hypo-ventilation or hypo-/hyper-capnia occurs.

The breath sampler device 10 is also configured and functional to be comfortable for the patient while enabling them to breathe either through their mouth and/or through their nose. Additionally, the breath sampler device 10 is designed and configured such that any components of it that are reusable do not come in contact with any biological contamination (bacteria or viruses) in the patient's breath. Further, it is to be appreciated that the breath sampler device 10 is designed and configured to accept a supply of clean air (e.g., from a clean air supply 14) such that any VBs present in the ambient room air are not captured by the device 10. The clean air supply was designed to provide a positive end expiratory pressure for the subject facilitating usage in patients with obstructive and restrictive lung disease. Furthermore, device 10 operates if this supply of clean air has additional oxygen added, up to and including 100% oxygen. This opens the device to use in patients requiring ventilatory support and usage in exposure experiments with spiked gases inhaled by the subjects such as common in diffusion tests. The materials of the breath sampler device 10 preferably do not emit any VBs that would affect the later in vitro analysis into the collected breath. In accordance with a preferred embodiment, the breath sampler device 10 captures up to four separate samples of the VBs in the patient's breath, whereafter each sample is readily and accurately identifiable to ensure that it is simple to track which patient it came from.

With regards to captured breath samples, the breath sampler device 10 is preferably configurable by the user to select the following for each pair of breath VOC samples: a) the portion of in or expired breath to be sampled (e.g. inspired air, oral air, alveolar breath, bronchiolar breath or total breath); and b) the volume of breath to be sampled for each of these fractions In accordance with a preferred embodiment, the breath sampler device 10 commences breath collection within a predetermined period of time (e.g., 30 seconds) of the patient breathing through it while recording its configuration and designated sensor and actuator readings during breath collection, which is preferably recorded to a central database including any warnings or errors that were generated during the breath collection process. During this initial time period the environmental VOCs are washed out and the breath collection software. The breath sampler device 10 also preferably provides a User Interface via a display unit to guide a device user through the breath collection process, confirm the results of the collection, and provide any warnings messages.

In accordance with the illustrated embodiments described herein, device 10 is preferably programmable to collect breath from a predetermined portion of in- or expired air in a patient's ventilatory system including nasopharynx, oropharynx, bronchi and alveoli. It is to be understood this is particularly advantageous because specific metabolic processes affect VBs differently in different portions of the breath. For instance, diseases in the alveoli leave VOCs in the last portion of breath exhaled by the patient whereas disease in the bronchioles leave VOCs in breath that is exhaled earlier in the exhalation. Furthermore this allows assessment of inspired air to quantify environmental exposures or standardised provocation and exposure experiments.

The breath sampler device 10 described herein is preferably readily assembled and disassembled, preferably without the use of tools, or specialty tools and is designed and configured such any components that are reusable do not come in contact with any biological contamination (microorganisms) in the patient's breath (with the exception being the sample collection tubes 20, in that after a breath collection, the tubes 20 are returned to a laboratory environment where they are fully recycled and cleaned after analysis).

The captured breath samples are preferably shipped for analysis in suitable protective packaging such that the breath samples captured in the tubes 20 do not require refrigeration or freezing during a shipping process.

In accordance with the described illustrated embodiments (and as mentioned above), the present invention breath sampler device 10 is configured and functional to capture a plurality of patient breath samples (e.g., 1 to 4). Preferably, two independent sample controls are captured, each one able to gather up to two samples in parallel with each other. For instance, for each sample control, the breath sampler device 10 preferably enables the user to configure which part of the breath to collect as follows: 1) how many samples are being collected (0, 1 or 2); 2) whether to use $CO_2$ or pressure to control the collection; 3) whether to start a collection pump when the control sensor reading is rising or falling; 4) the percentage sensor reading threshold at which to start the collection; 5) whether to stop the pump when the control sensor reading is rising or falling; 6) the percentage sensor reading threshold at which to stop the collection; and 7) the volume of breath to be collected.

The breath sampler device 10 is preferably configured and functional such that it records the volume collected in each of the sample tube (e.g., sorbent tube 20) and stops the collection at the end of the collection event in which the required volume is reached. For instance, when the breath sampler device 10 is collecting two samples on one sampling channel, the collected breath sample volume is split evenly between the two samples in respective tubes. In accordance with a preferred embodiment, the breath sampler device 10 is preferably preconfigured with settings prescribing, and controlling operation of the device 10 to capture one of alveolar breath, bronchial breath and whole breath.

Turning now descriptively to the drawings, in which similar reference characters denote similar elements throughout the several views, FIG. 1 depicts a system for collection of volatile biomarkers, or other animal body, includes a vapor sampling device 10 and a separate detector/analyzer apparatus 12, a clean air supply source 14 and external computing device 16 to be coupled to device 10. It is to be appreciated that for ease of description purposes, the illustrated embodiments described herein are discussed in reference to a vapor sampling device 10, such as a breath sampler, for collecting breath samples from a human patient to collect volatile biomarkers for biomedical purposes. However, the illustrated embodiments are not to be understood to be limited thereto as they may encompass vapor sampling devices for capturing other vapors from a body such as those that emit from stool and urine, as could be of interest for detecting the presence of colon cancer and prostate cancer. Additionally, while FIG. 1 depicts the vapor sampling device 10, detector/analyzer apparatus 12, the clean air supply source 14 and external computing device 16 as separate units, the illustrated embodiments are not to be understood to be limited thereto as they also may encompass a device 10 that incorporates one or more the aforesaid ancillary components.

Figure 2A:
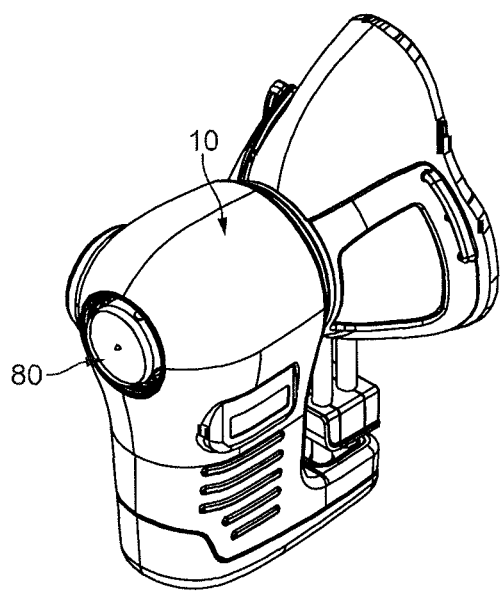
FIGS. 2A and 2B illustrate a perspective (FIG. 2A) and cross-sectional view (FIG. 2B) of a breath sampler device of an embodiment of the present invention.
Figure 2B:
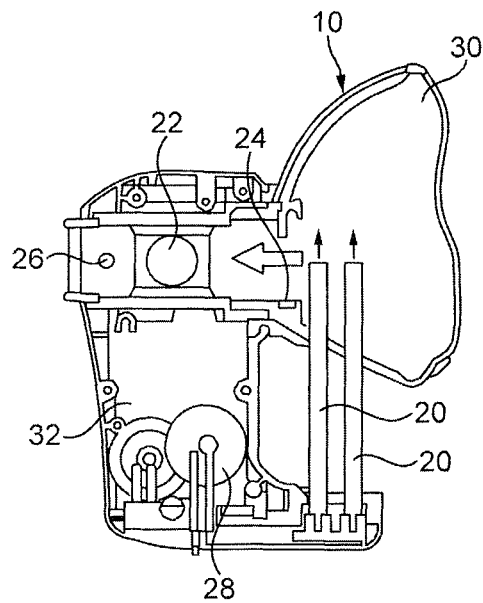
Figure 5:
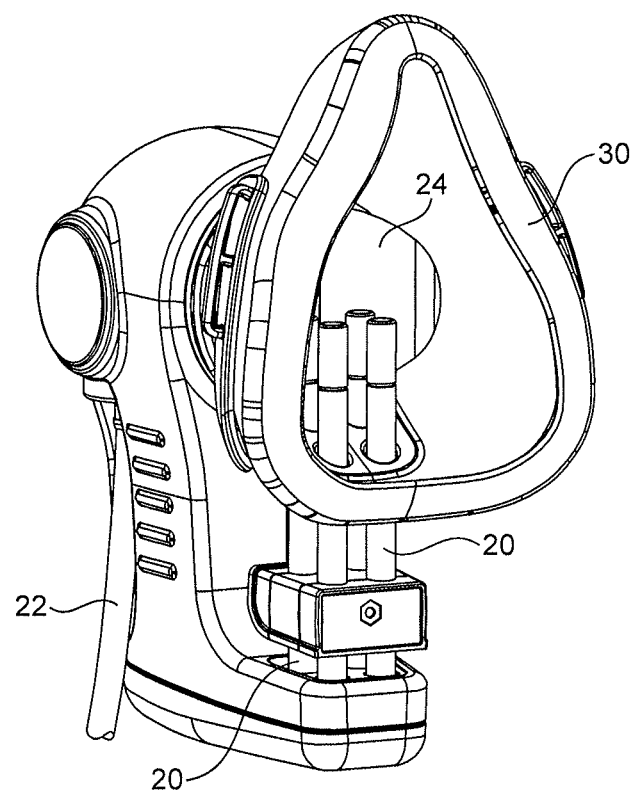
FIGS. 5-7 illustrate various perspective views of the device of FIGS. 2A and 2B.
Figure 6:
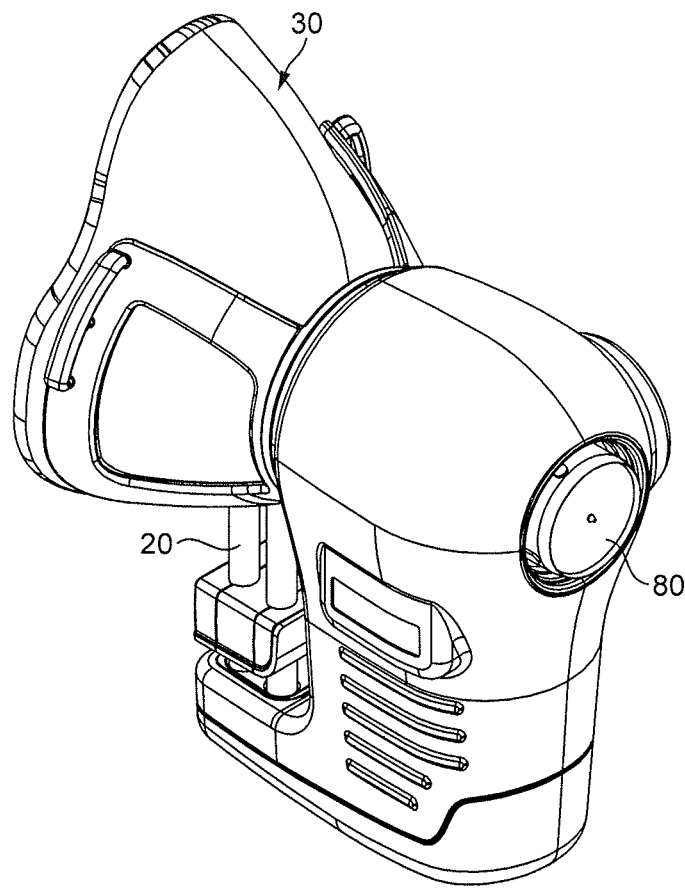
Figure 7:
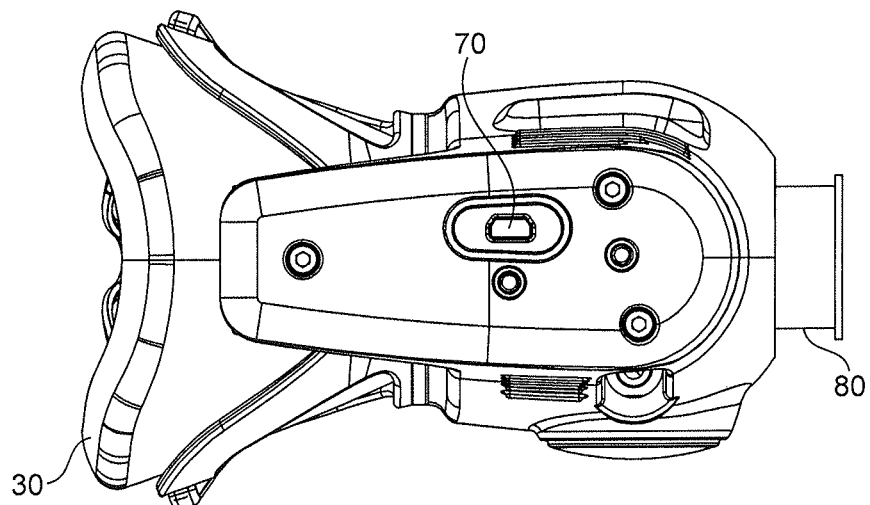

With simultaneous reference to FIGS. 2A and 2B, depicted is an illustrative embodiment of a breath sampling device 10 (FIG. 2A) and its cross-sectional view (FIG. 2B). Additionally views of the device 10 are also shown in FIGS. 5-7.

What is described below is a vapor sample (e.g., a breath sample), is obtained from the patient via the breath sampling device 10, which is then captured and held in sorbent tubes 20. The sorbent tubes 20 are subsequently removed from the breath sampling device 10 and disposed within a detector/analyzer apparatus 12, which is functional to extract the breath sample from the sorbent tube 20 so as to preferably perform a FAIMs analysis thereon to detect VBs in the breath sample to diagnosis lung cancer. It is to be understood device 10 in FIG. 2 depicts two (2) sorbent tubes, but it is to be appreciated device 10 may be configured to accommodate any desirable number of sorbent tubes 20.

Figure 9:
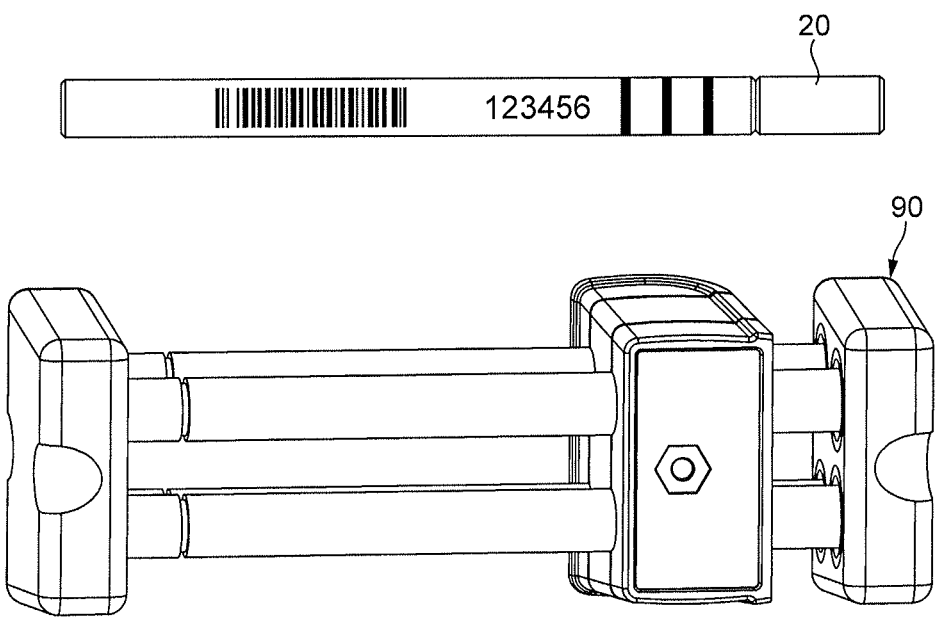
FIG. 9 illustrates a perspective view of a sorbent tube and a packaging container used to transport the sorbent tube used with the device of FIGS. 2A and 2B.

As mentioned above, the device 10 collects VBs in sorbent tubes 20 (FIG. 9). For instance, a sorbent tube 20 used with device 10 is preferably a stainless steel tube which is approximately 3 inches long and has a ¼ inch diameter containing a sorbent material (e.g., similar to activated carbon) that is specifically designed to absorb VBs and to then re-emit them when the tube 20 is preferably heated in detector/analyzer apparatus 12. It is to be appreciated the tubes 20 can be stored for several days and can be shipped via mail and package carriers via preferably a packaging container 40 (FIG. 9). It is to be understood the sorbent tubes 20 are preferably glass coated stainless steel tubes packed with absorbent resins (sorbents) designed to trap VBs. When the tubes are subsequently heated in a laboratory environment 12, they release the VBs allowing them to be analyzed. As shown in the FIGS. 2, 5 and 6, the sorbent tubes 20 preferably push through holes formed in the mask 30 and then connect into the device frame at the bottom portion of the device 10. The sorbent tubes 20 are preferably held via a clamp device to simplify installation and removal from device 10. The sorbent tubes 20 are preferably mounted unevenly (e.g., 12 mm spacing at a front portion and 14 mm at a back portion of device 10) so that the block of the sorbent tubes 20 will only fit into the breath capture unit via a designed orientation.

For instance, the sorbent tubes 20 are each preferably hollow glass passivated stainless steel tubes dimensioned to be 89 mm long by 6.4 mm (3.5" by ¼") OD packed with Tenax GR and Carbograph 5TD, which is the sorbent mix adapted to trap VOCs from a patient's breath. After a breath sample is collected in the tubes 20, they are then sealed, removed from device 10 for subsequent analysis in analytical/detection device 12 wherein the tubes 20 are preferably heated to release the VOCs into the analytical instrument 12. It is to be understood sorbent material is retained at each end of the tube 20 by glass wadding and tightly fitting stainless steel gauze at each end of the tube 20. This ensures that the sorbent material cannot escape from the tube 20. With reference to FIG. 9, each sorbent tube 20 is preferably labelled with a unique serial number and bar code for easy identification and an arrow indicator is preferably provided to show the direction of breath flow. Also shown in FIG. 9 is a packaging transport device 40 used to transport tubes 20 removed from the breath sample device 10 to a remotely located analytical/detection device 12 preferably in a laboratory environment.

With regards to construction and assembly of device 10, it preferably includes a $CO_2$ and pressure sensor 22, replaceable bacterial filter 24, clean air supply 26, pump(s) 28, a replaceable flexible face mask 30 and a control board 32 for controlling operation of the aforesaid primary components of device 10. The functionality of the aforesaid primary components are further discussed below, and the control board 32 is to be understood to include one or more of the system components shown in FIG. 11 (as also described below).

During a tidal breathing procedure, the $CO_2$ and pressure sensor 22 preferably monitors breathing adequacy and frequency while pump(s) 28 facilitate passage, and capture, of a portion of a patient's breath in the sorbent tubes 20. The sensor 22 is further preferably configured to measure pressure and temperature within the mask 30 as well as $CO_2$ level in the mask 30. For instance, the sensor 22 may include a $CO_2$ sensor 22 component (e.g., such as a readily available Sprint™ IR-W-X type sensor for measuring/detecting a level of $CO_2$) in the mask 30, which may be optionally used for selecting a portion of the patient's breath the device 10 collects in sorbent tubes 20 (as described herein).

In accordance with an illustrated embodiment, the pressure sensor component of sensor 22 may be a readily available Bosch™ BMP280 combined pressure temperature sensor configured and functional to monitor the pressure in the mask 30, which as described herein is utilized for selecting a predetermined portion of a patient's breath to capture (via the sorbent tubes 20). Preferably, device 10 contains six absolute pressure temperature sensors 22. For instance, sensor 22 is mounted preferably in the mask 30 to measure the pressure and temperature of the patient's breath. Another sensor 22 is preferably mounted on the inlet and on the outlet of each pump 28 and the other sensor(s) monitor ambient pressure and temperature regarding the device 10. For instance, the aforesaid sensors 22 are utilized such that the mask pressure sensor 22 measures the pressure in the mask, which is utilized to determine the correct points to switch on and off the collection pumps 28 to collect a designated portion of the patient's breath (e.g. alveolar) for capture in the sorbent tubes 20. The $CO_2$ sensor 22 measures the $CO_2$ level in the patient's breath and is an alternative to pressure for the pump control. It is noted that the difference between the mask pressure sensor and the pump inlet pressure sensor is preferably utilized to detect leaks and blockages in the sorbent tube 20 and associated air passageways, and to detect if a sorbent tube 20 is not properly fitted in device 10. It is further to be understood that the difference between the pump inlet pressure and the pump outlet pressure is also utilized to determine if a pump 28 is working properly, to check for blockages or leaks, and to measure the flow rate through each pump 28. The flow rate is integrated to determine the amount of breath collected from a patient. It is additionally to be further understood that the difference between the pump outlet pressure and ambient pressure may also be used to determine if a pump outlet is blocked.

In accordance with a preferred embodiment of the present invention, the sensors 22 have the following specifications:

| Parameter | Value | Notes |
| --- | --- | --- |
| Pressure Range | 300-1,100 mBar | |
| Absolute Accuracy | ±1.0 mBar | Over 950-1,050 hPa |
| Relative accuracy | ±0.12 mBar | |
| Temperature Range | −40 to +85° C. | |
| Pressure Resolution | 0.01 mBar | |
| Temperature Resolution | 0.1° C. | |
| Measurement Rate (slowest mode) | 23.1 Hz | Worst Case |

It is to be understood that the output of the aforesaid sensors 22 is preferably digital such that full measurement specification may be provided to the aforesaid software executing on the external computing device 16.

During testing of a preferred embodiment of the device 10, it was determined the pressure range in the mask 30 was typically ±500 Pa (±5 mBar) either side of atmospheric. To control the sampling accuracy when using pressure as the input, the breath sampler device 10 is preferably configured and functional to establish the maximum and minimum pressure in each breathing cycle, and then be able to resolve the maximum and minimum pressure in each breathing cycle. In operation the following specifications for mask pressure measurement is preferably:

Measurement Range: 790-1,100 mBar
Relative Accuracy: ±100 Pa (±1 mBar)
Resolution: 10 Pa (±0.1 mBar)

It is to be appreciated that 790 mBar is the expected atmospheric pressure at the highest city in Europe and America (Santa Fe, N. Mex. 2,213 m). The highest atmospheric pressure ever measured on earth is 1083 mBar (Agata, Siberia, Russia Dec. 31, 1968). Thus, it is to be understood the relative accuracy is the accuracy with which the mask pressure sensor 22 can measure the difference between the pressure in the mask 30 and the pressure in the room (as measured by the environmental pressure sensor) once the offset between the two has been corrected for (if required), preferably with the mask 30 not fitted to the patient and the external air supply 14 switched off.

With regards to the $CO_2$ sensor 22, illustrative specifications include:

| Parameter | Value |
| --- | --- |
| Measurement Range | 0-20% CO2 |
| Absolute Accuracy | ±70 ppm ± 5% of reading |
| Temperature Range | 0 to +50° C. |
| Operating Pressure Range | 950 mbar to 10 bar |
| Measurement Rate | 20 Hz |
| Resolution | 0.0001% |

It is noted the output of the $CO_2$ sensor 22 is preferably in ppm such that known conversion factors are required to convert acquired data to percent $CO_2$. It is also noted that a requirement for $CO_2$ sensing is that the device 10 preferably reads mask $CO_2$ in the range 0-10% $CO_2$ at 5 Hz to a minimum resolution of 0.05% and to an overall accuracy of ±0.5% $CO_2$ over the normal breath range of 0-5% $CO_2$. The aforesaid $CO_2$ sensor 22 preferably has a resolution of 0.1 ppm or 10-5% and a "worst case" absolute accuracy of ±70 ppm±5% of 5%=±0.257% $CO_2$.

With regards to $CO_2$ measurement and accuracy, the $CO_2$ concentration is expected to be less than 0.1% in the input air and approximately 4.5% in the exhaled breath. As with pressure to control the sampling accurately when using $CO_2$ as an input, the breath sampler device 10 is preferably configured and functional to establish the minimum and maximum $CO_2$ levels for each breathing cycle and to resolve between the minimum and maximum $CO_2$ levels for each breathing cycle. In a preferred embodiment, the device has a detection rate as follows:

Measurement range: 0-10% (to provide cover for high levels)
Measurement accuracy: ±0.4% $CO_2$ over 0-5% (10% of expected range)
Resolution: 0.04% $CO_2$ (one percent of the expected range)

With regards now to the replaceable bacterial filter 24 and flexible face mask 30, they preferably prevent instances of cross-contamination relative to a patient's breath. The biological filter 24 is preferably mounted in the mask 30 and is configured and constructed to ensure that all biological contamination in the patient's breath (e.g., bacteria or viruses) come in contact with the mask 30 and the filter 24 (both of which are one-time use) and the sorbent tubes 20 (which are preferably baked at around 300° C. before each patient). The face mask 30 is preferably formed of silicone material designed for both patient comfort, and to contact the sorbent tubes 20, the biological filter 24 and a portion of the housing for device 10 (as shown in FIG. 2). It is noted the mask 30 does not obscure a patient's vision while permitting the patient to breathe through their mouth and/or nose.

With further regards to cross-contamination, device 10 is fitted with a clean air supply valve 26 which intakes clean air from an external source 14 so as to avoid contamination of the patient's breath with the ambient air surrounding device 10 and the patient. In the illustrated embodiment of FIG. 2, device 10 is configured to contain a pair of sorbent tubes 20, wherein each sorbent tube 20 may be independently gated to collect different breath fractions during a same breath collection event. It is to be understood the sorbent tubes 20 are to contain patient breath samples which are to be analyzed offline (separate from device 10) on numerous testing platforms, including (and not limited to) GC-MS and GC-FAIMS platforms in a laboratory environment 12.

It is also to be understood, in an alternative embodiment, device 10 may be coupled directly to a detector/analyzer apparatus 12 thus obviating the need to separately remove the sorbent tubes 20. It is to be further appreciated that four calibrated orifice plates may preferably be provided in device 10 to balance the flow through the sorbent tubes 20 (FIG. 7).

With regards to pump(s) 28, it is to be understood two computer controlled pumps 28 are provided in the illustrated embodiment, each configured to draw a patient's breath through the sorbent tubes 20 (e.g., one pump 28 for each pair of tubes 20). Each pump 28 preferably has an absolute pressure sensor mounted directly upstream of it and downstream of it to determine the flow rate through the pump 28 and to detect leaks and blockages (as mentioned above). A microprocessor is preferably provided in the control board 32 to provide a level of control of the pumps 28 and to read sensors and to provide this information over a USB connection 70 (FIG. 7) to preferably an externally computing device 16 (FIG. 1) (e.g., such as a desktop, laptop, tablet or computing type device). It is to be appreciated the USB connection 70 further facilities electrical power delivery to the device 10. It is to be further understood software is preferably executing on the aforementioned external computing device 16 to control data sampling and to record results regarding patient breath samples. It is also to be understood the aforementioned microprocessor 32 is coupled to associated drive electronics configured to operate the pumps 28, read the sensors 22 and communicate such data to said external computing device 16.

As previously mentioned, the device 10 of the illustrated embodiment is preferably controlled by software executing on an external computing device 16. With regards to the software, it is to be understood its execution affects communication via the USB connection 70 with the pumps 28 functional to communicate with and read the sensors provided in the device 10 (e.g., sensors 22); control the pumps 28 to turn on and off at the designated times to collect a selected portion of a patient's breath; track an amount of breath collected in each sorbent tube 20 and stop collection when an ample amount of patient's breath has been collected; and guide an operator/user (e.g., medical professional), preferably via a user display or GUI provide on the external computing device 16 or device 10, through a breath collection process with the provision of appropriate feedback.

With regards to the present illustrated embodiment, it is to be further understood, each pump 28 preferably has a Bosch™ BMP 280 pressure sensor mounted upstream and just downstream of it, which pressure sensors are used to determine the flow rate through the pump 28 and to detect whether the pump 28 and/or a sorbent tube 20 is leaking or blocked. It is to be appreciated the pumps 28 are preferably configured to exhaust to the ambient air surrounding device 10. Additionally, orifice plates (as shown in FIG. 7) having small accurate flow restrictors are provided on the device 10 configured to provide an accurate flow resistance positioning the pumps 28 into a correct portion of their operating curve to mitigate the variation in the flow between the sorbent tubes 20 on the pumps 28 caused by differences in their flow resistance.

Figure 3:
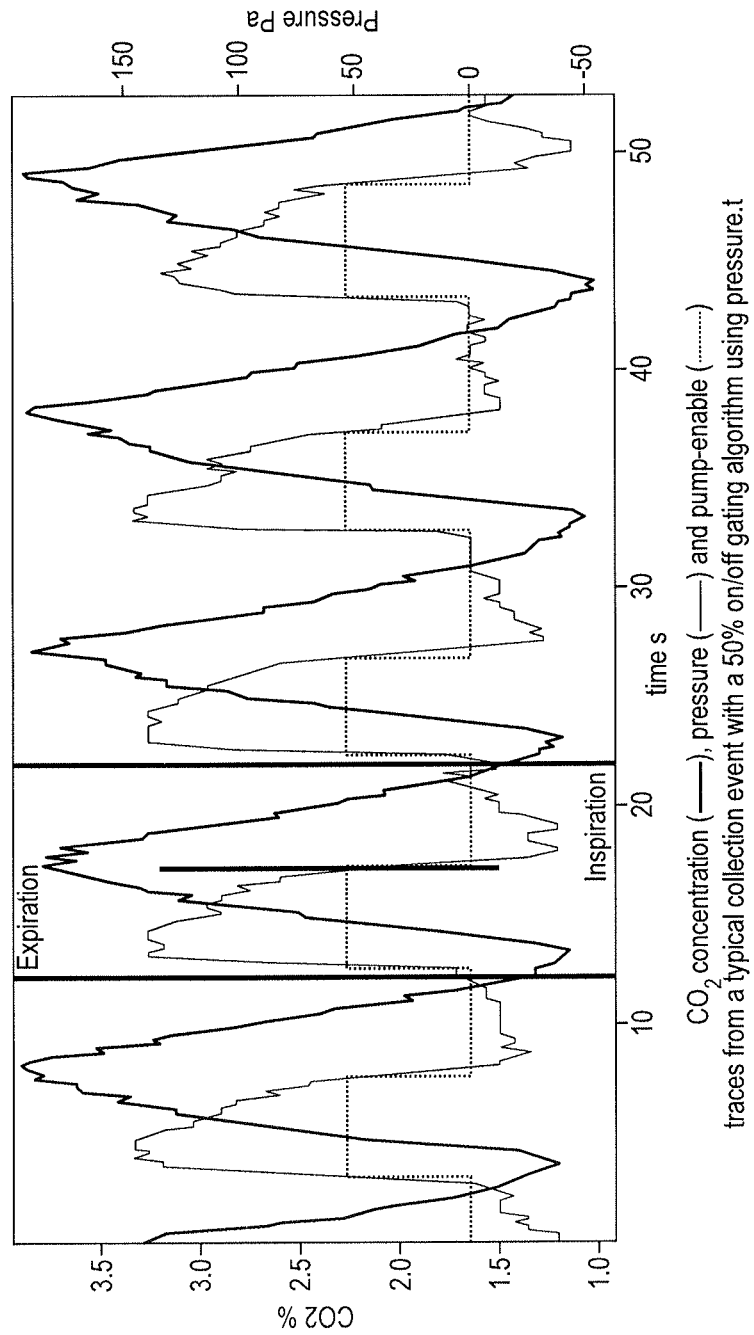
FIG. 3 and FIGS. 4A and 4B depict analysis of test data regarding capture of a patient's breath using the device of FIGS. 2A and 2B and system of FIG. 1.
Figure 4A:
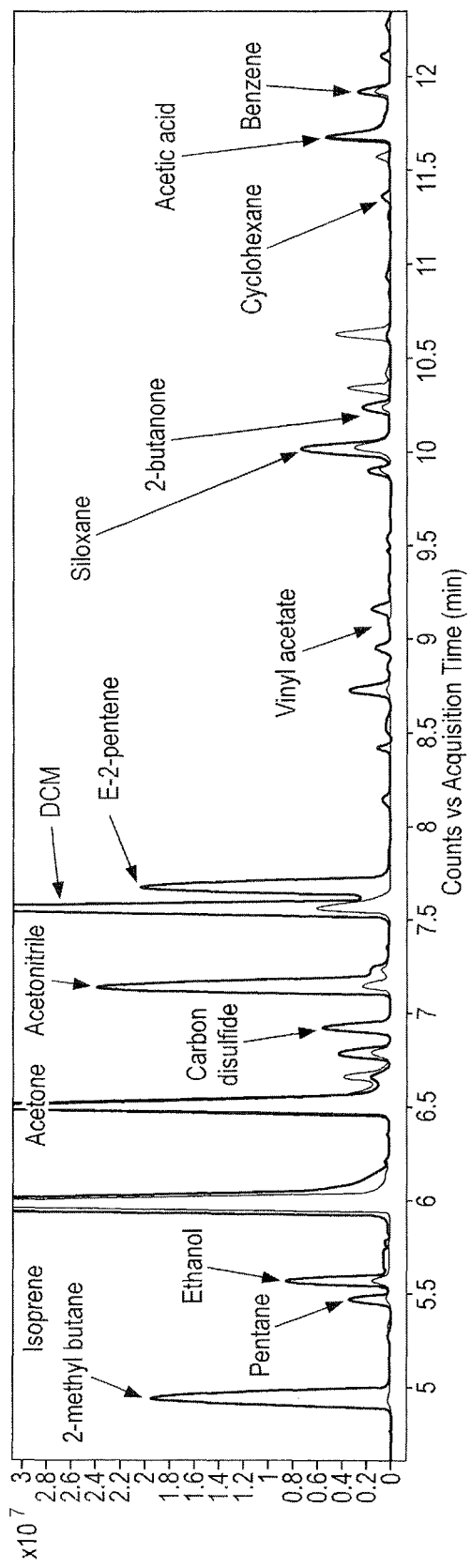
Figure 4B:
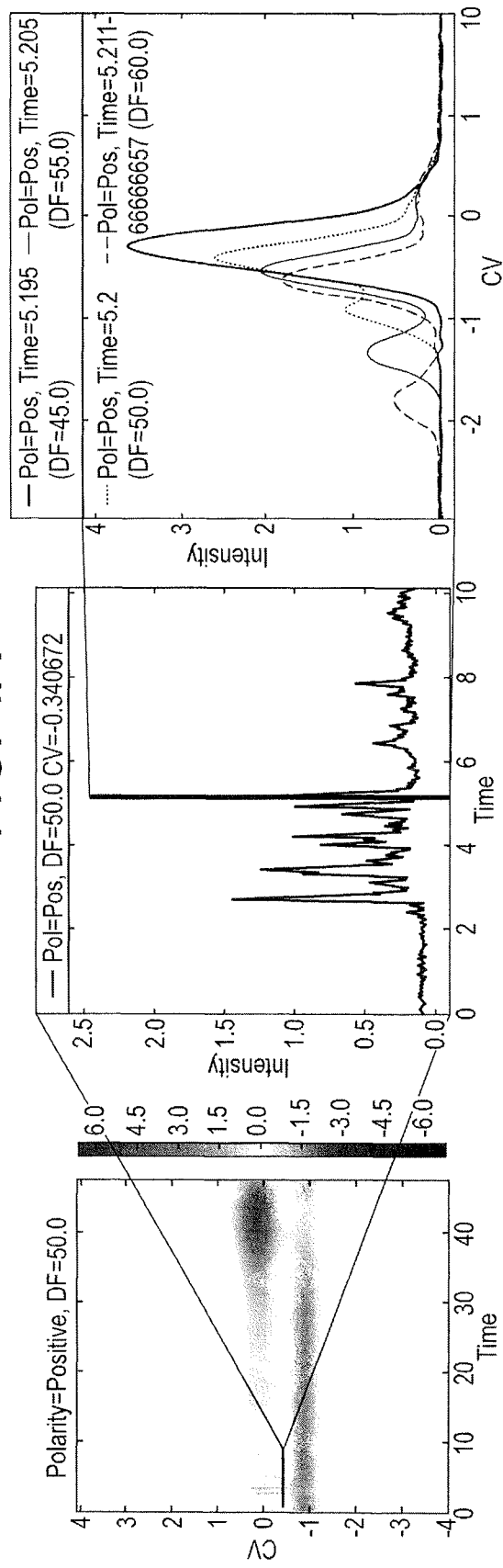

With reference now to FIGS. 3 and 4, illustrated is actual test result data regarding usage of device 10 with one hundred (100) patients. FIG. 3 illustrates $CO_2$ concentration, pressure and pump-enable traces from a collection event with a 50% on/off gating algorithm using pressure. And FIG. 4A illustrates GC-MS results from breath samples including retention time matched and NIST identification while FIG. 4B illustrates GC-FAIMS quality control.

Figure 8:
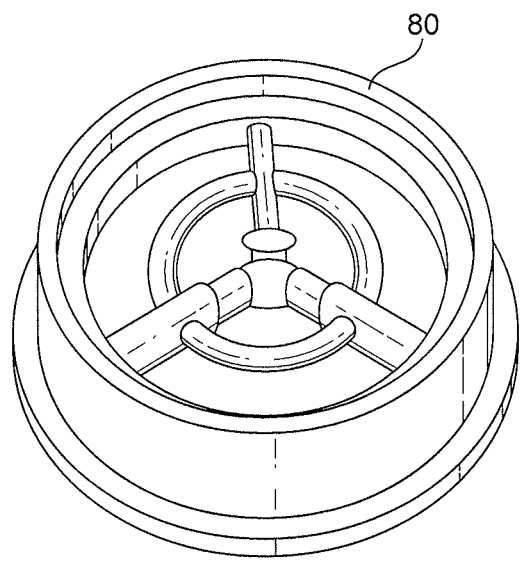
FIG. 8 illustrates a one-way valve used in the device of FIGS. 2A and 2B.

Continuing with operation of the device 10, it is to be understood a patient fits the disposable silicone mask 30 to the patient's face preferably configured to allow them to breathe through their nose and/or mouth. A head strap is preferably fitted to the face mask 30 to hold the unit in place on the patient. The biological filter 24 is preferably provided at the outlet portion of the mask 30 designed to prevent contamination from the patient's breath coming in contact with the breath sampler device 10. As mentioned above, a clean air supply 14 (via valve 26) enables the patient to breath air that is preferably free of VBs that might be present in the ambient room air surrounding device 10, as these would contaminate the breath sample. It is to be understood the outlet portion of the mask 30 includes a one-way valve 80 (FIG. 8) permitting the patient to breathe out to the room while inhaling (scrubbed) clean air, via its coupling to a clean air supply source 14 (via valve 26). It is to be understood the aforementioned one-way valve 80 is preferably a mechanical unit consisting of a plastic membrane that permits air out of the device 10 but does not permit air in.

The breath sampler device 10 preferably starts the collection within a predetermined time from device activation (e.g., 30 seconds) preferably triggered by a patient breathing through it and subsequently confirms to the medical professional attending operation of the device 10 that the collection process is complete. Preferably, a medical professional is able to prescribed a maximum time for the patient breath collection, and if the required volume of breath has not be collected within the prescribed time, collection ceases (e.g., an error message may be displayed).

Figure 10:
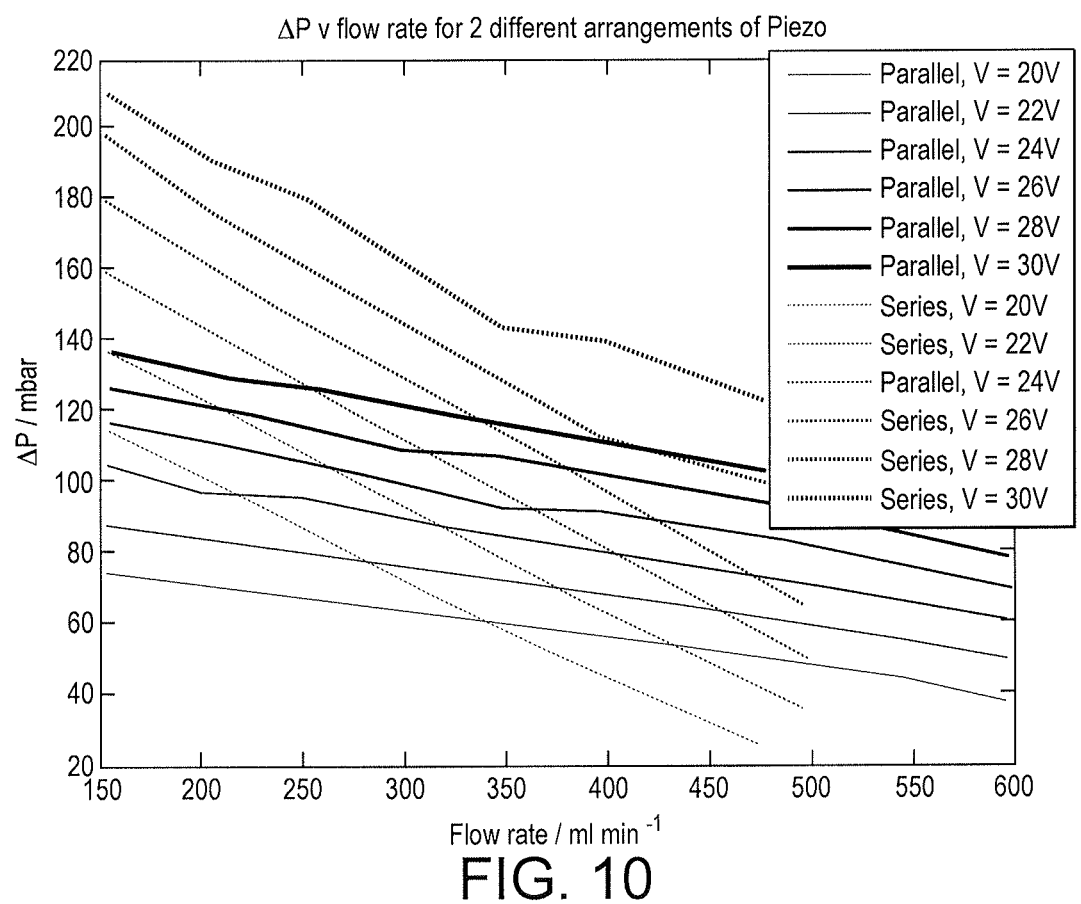
FIG. 10 illustrates a chart depicting data regarding operation of pumps used in the device of FIGS. 2A and 2B.

With regards to the breath flow rate through the sorbent tubes 20, it is to be understood if it is too slow the patient then has to spend too long a time breathing into the mask 30, and if the breath flow rate is too fast then the most volatile chemicals are likely lost by not being captured within the sorbent tubes 20. Test data has demonstrated that 200-300 mL/min is an optimum rate through each tube 20 whereby the flow rate generates a pressure drop across the sorbent tube 20 of 42.5 mBar. It is noted that the collected breath volume is a compromise between patient comfort and having enough time to collect VOCs to analyze. In accordance with an illustrated embodiment, 1.2 litres on each tube 20 is optimal, requiring a test length of approximately 6 minutes. It is noted though that the actual collected volume and flow rate may be chosen by a medical professional user of device 10. Regarding operation of the pumps 28, each pump has a flow characteristic as shown in FIG. 10. It is to be appreciated that for optimum collection, the sorbent tubes 20 require a flow rate of up to 300 mL/min each, thus each pump 28 should deliver up to 600 mL/min. Additionally as shown in the pump flow characteristics of FIG. 10, each pump 28 preferably has two separate pump units that can be plumbed in series or in parallel, wherein the graph depicted in FIG. 10 shows a parallel connection is preferred.

With further regards to operation of the breath sampler device 10, it is preferably required to collect 95% of the patient's breath that the medical professional expects and no more than 5% of other breath. As mentioned throughout this description, the portion of a patient's breath is collected and determined by when in each breath cycle the sample collection pump 28 is turned on and off. The accuracy of this is determined by: i) the accuracy of the mask pressure or $CO_2$ measurement; ii) the latency in reading the sensors 22; and iii) the latency in switching the pumps 28 on or off. In operation, typical breathing rates in adults are 16-20 breaths per minute, extending to 10-30 breaths per minute for patient's over 80 years of age. Therefore, in use, the breath sampler device 10 is preferably configured and adapted to operate from 8-30 breaths per minute, corresponding to a breath every 2.0-7.5 seconds. Thus, to satisfy these operating parameters, 95% of the correct breath is preferably collected and only 5% of incorrect requires a timing accuracy of ±2.5% of a breath for both the start and end of breath collection. Accordingly, execution of the firmware embedded in device 10 requires that: the firmware reads the control sensor (mask pressure or $CO_2$); sends readings to the externally coupled computing device 16 (preferably via USB connection, or wireless connection). And the PC software executing on the externally connected computing device 16 reads the aforesaid captured data to determine the time to switch the state of the pump between on/off, which software also sends a message to the device embedded firmware to execute operation of the pumps 28.

Regarding the breath flow measurement accuracy for device 10, the device is configured and functional to derive the flow rate through each sample collector preferably in the range 0-300 mL/min at 5 Hz with an accuracy of ±5% to meet the requirement that the volume of breath collected is accurate to ±5%. The flow rate is preferably determined by measuring the pressure drop across the pumps 28. The flow accuracy is therefore generated by the accuracy of the pressure measurement and the accuracy of the flow calibration. The approximate total error expected between the two pressure readings (pump upstream and pump downstream) is ±2.0 mBar (as indicated above) which is equivalent to a flow measurement error of ±0.67 mL/min or ±0.34% of the expected flow rate of around 200 mL/min. Thus, it is evident that there is therefore a requirement that the flow characteristics of each system are calibrated accurate to better than ±4.6%.

In operation, the flow path for the breath samples (air) through the sorbent tubes 20 is as follows: first, the collection of breath (air) commences in the mask 30 where there is preferably a pressure sensor ($P_{mask}$). The collected air from the patient then goes through the sorbent tubes 20, and then through an orifice plate (FIG. 7). Pressure is measured upstream of the pump 28 ($P_{up}$), which passes through the pump 28. The pressure is also measured downstream of the pump ($P_{Down}$) and then vented to atmosphere.

It is to be appreciated that the pressure rise across each pump 28 is a function of the flow through it (as mentioned above) and as a result by comparing the pressure rise across a pump 28 with that expected for the voltage applied it facilities the detection of air blockages in device 10. For example, at 24V the expected pressure rise is around 80 mBar at 500 mL/min (the expected flow), but when blocked, the pressure rise will be 110 mBar. The pressure sensors can measure the pressure rise to ±0.24 mBar. It is noted this same method is used to detect leaks. That is, if there is a leak where a sorbent tube 20 connects to the breath capture unit (e.g., detected by the change in the pressures). Using this process, the differences in the flow resistance of a sorbent tube 20 compared with another tube 20 connected to the same pump 28 is thus evident.

In operation, it is further noted that each tube 20 has a Lee orifice plate in series with it and the pressure drop across these plates balances the flow between the two tubes 20 such that approximately a 10% difference in flow resistance only causes a 4.8% error in the flow in that tube and a 0.9% error in the other tube. Thus, device 10 is configured and functional to detect when the wrong number of sorbent tubes 20 has been fitted as the flow rate will be half (or twice) that is expected, this pressure drop will be incorrect.

Discussion is now provided regarding the process the device 10 performs regarding verification that the patient breath sample it has collected is correct. Preferably, during operation of the device 10, the following device readings are monitored to determine whether they reside within pre-defined limits: 1) the patient's breathing rate; 2) the $CO_2$ level during exhalation; 3) the pressure during inhalation; and 4) the pressure during exhalation. The device 10 preferably performs a routine that checks that the pumps 28 have been turned on and off correctly throughout the collection and that there are no leaks or blockages in the breath collection path and whether an air blockage present in the sample collection path which would compromise the capture of patient breath samples.

Figure 11:
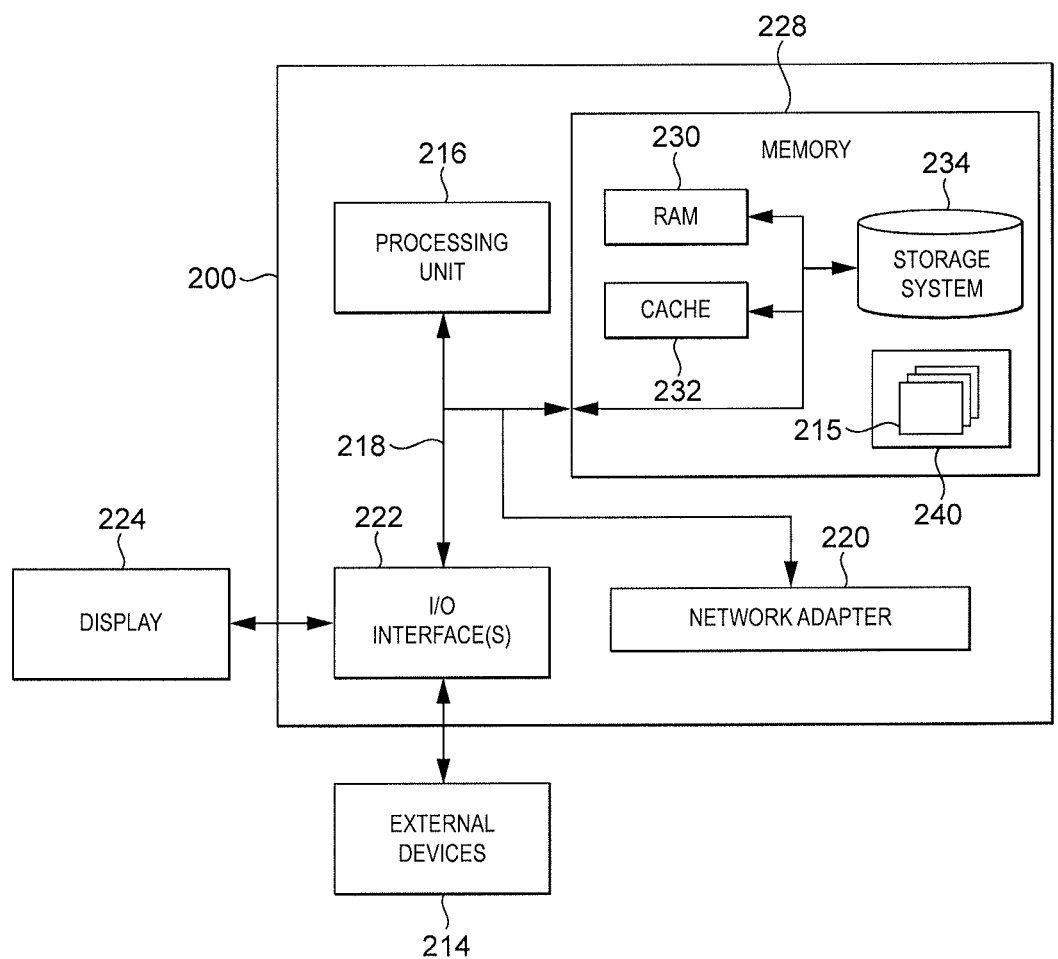
FIG. 11 illustrates an example computer device/system which may be used in the device of FIGS. 2A and 2B.
Figure 12A:
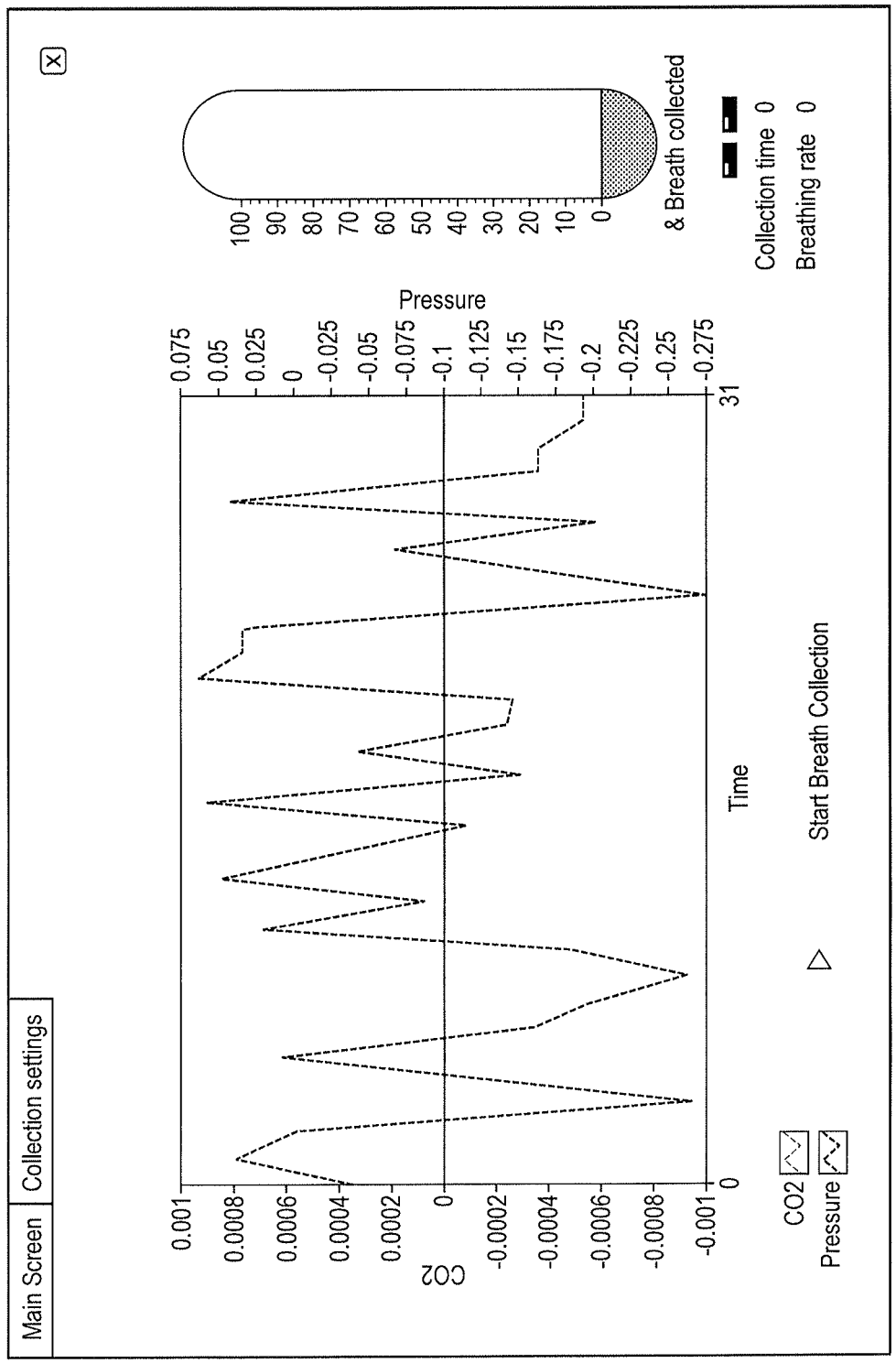
FIGS. 12A-12F illustrate a user interface provided by the computer device/system and various settings, options and guidance provided to the user.
Figure 12B:
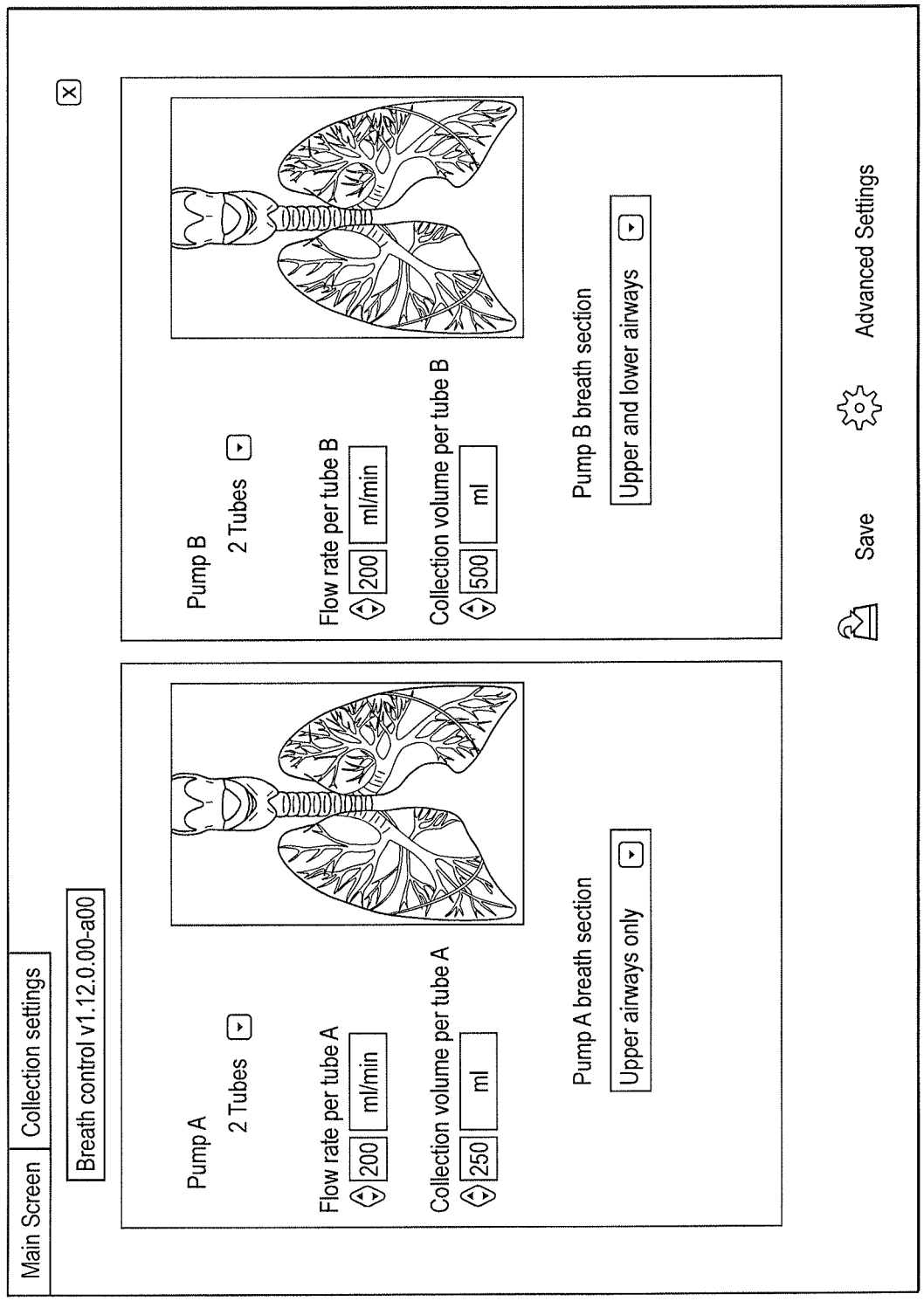
Figure 12C:
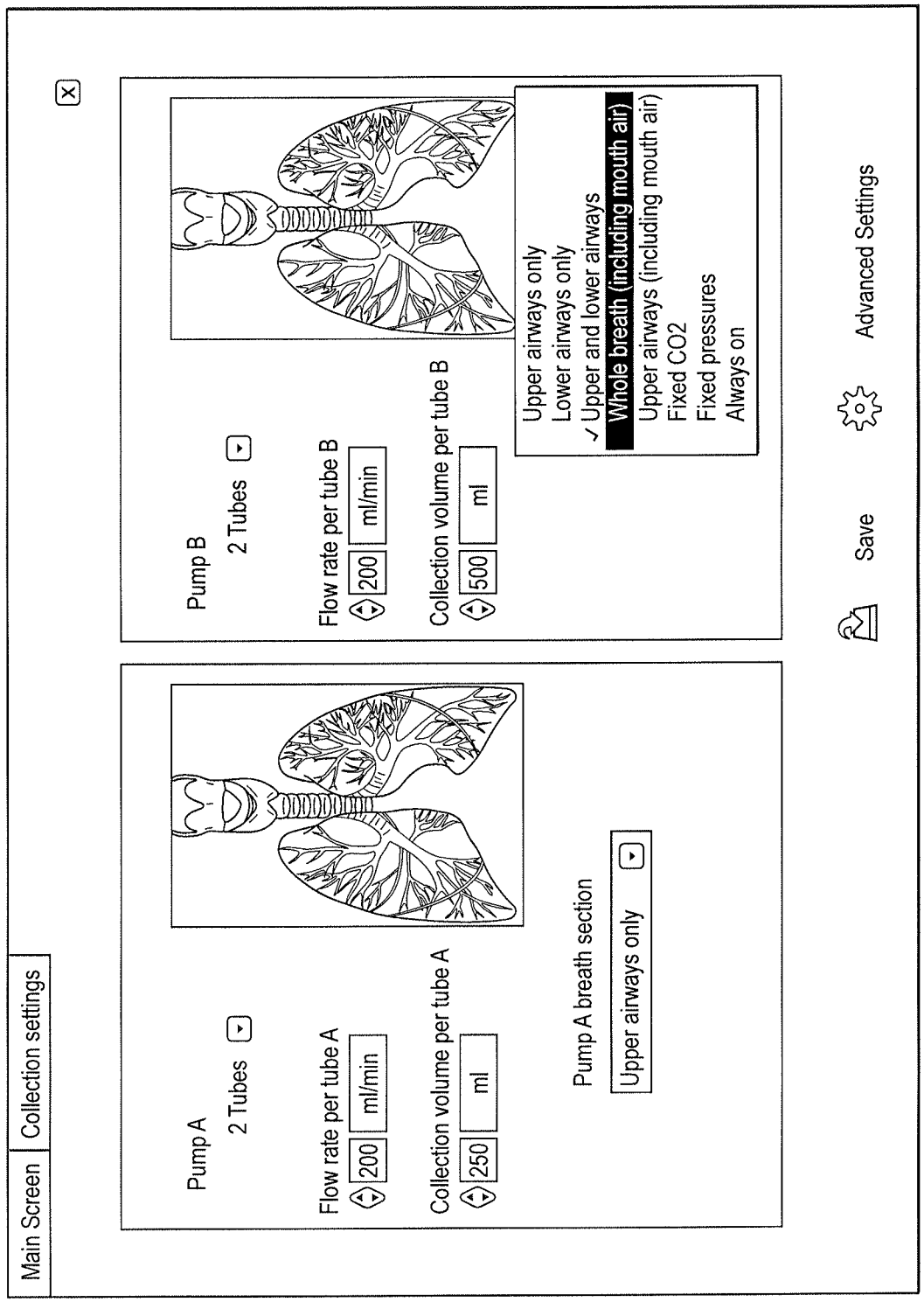
Figure 12D:
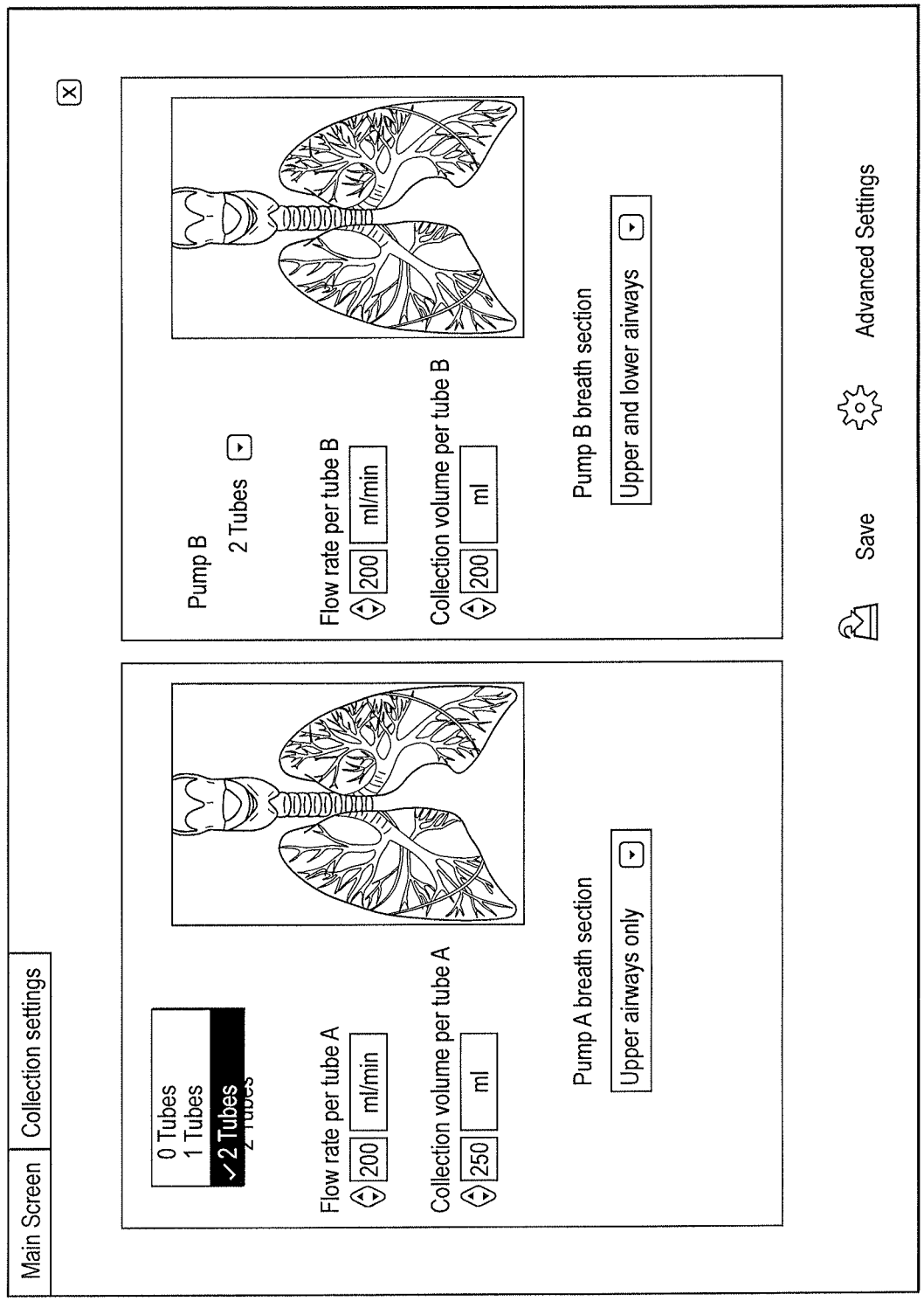
Figure 12E:
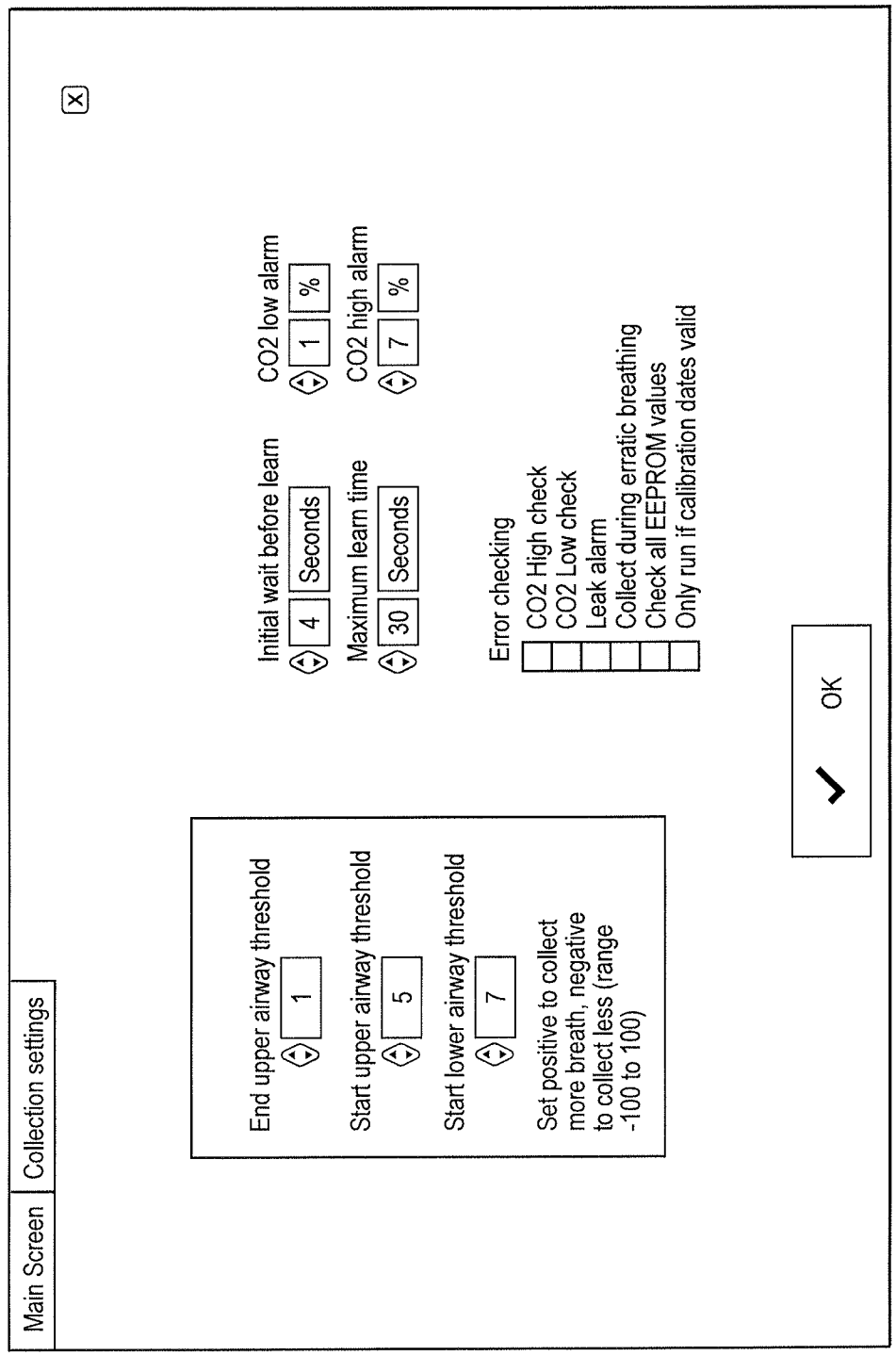
Figure 12F:
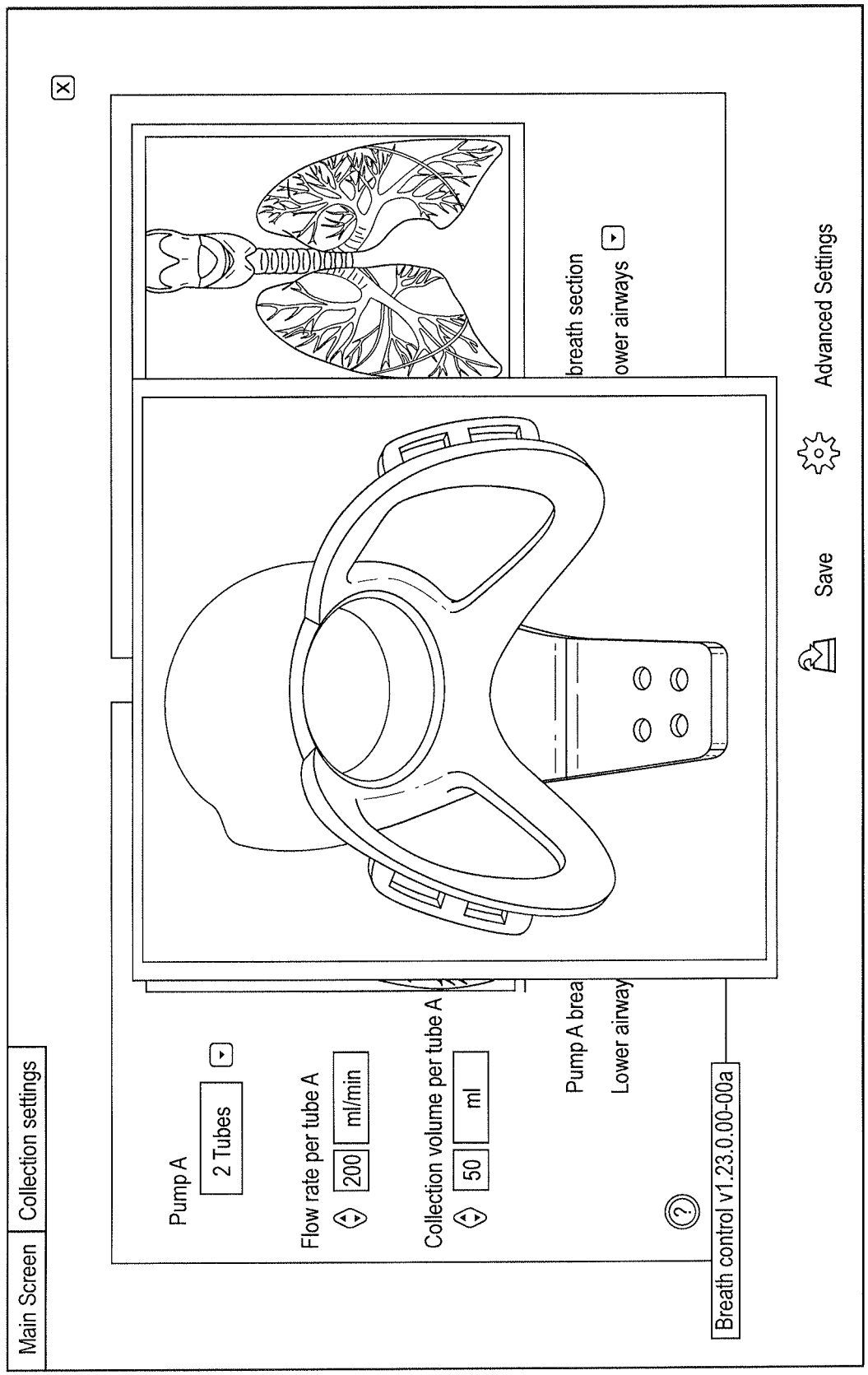

With description of one or more illustrated embodiments of device 10 being described above with reference to FIGS. 1-10, description now will be provided regarding the control board 32 and associated computing components and systems used in conjunction with operation of device 10. With reference now to FIG. 11, shown is a computer system 200, the components of which may be included in device 10 (e.g., control board 32).

The components of system 200 may include, but are not limited to, one or more processors or processing units 216, a system memory 228, and a bus 218 that couples various system components including system memory 228 to processor 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing device 200 typically includes a variety of computer system readable media. Such media may be any available media that is accessible by device 200, and it includes both volatile and non-volatile media, removable and non-removable media.

System memory 228 can include computer system readable media in the form of volatile memory, such as random access memory (RAM) 230 and/or cache memory 232. Computing device 200 may further include other removable/non-removable, volatile/non-volatile computer system storage media. By way of example only, storage system 234 can be provided for reading from and writing to a non-removable, non-volatile magnetic media and/or Solid State Drives (SSD) (not shown and typically called a "hard drive"). Although not shown, a magnetic disk drive for reading from and writing to a removable, non-volatile magnetic disk, and an optical disk drive for reading from or writing to a removable, non-volatile optical disk such as a CD-ROM, DVD-ROM or other optical media may be associated with system 200. In such instances, each can be connected to bus 218 by one or more data media interfaces. Memory 228 may include at least one program product having a set (e.g., at least one) of program modules that are configured to carry out the functions of embodiments of device 10 described herein.

Program/utility 240, having a set (at least one) of program modules 215, such as underwriting module, may be stored in memory 228 by way of example, and not limitation, as well as an operating system, one or more application programs, other program modules, and program data. Each of the operating system, one or more application programs, other program modules, and program data or some combination thereof, may include an implementation of a networking environment. Program modules 215 generally carry out the functions and/or methodologies of embodiments of the invention as described herein.

Device 200 may also communicate with one or more external devices 214 such as a keyboard, a pointing device, a display 224, etc.; one or more devices that enable a user to interact with computing device 200; and/or any devices (e.g., network card, modem, etc.) that enable computing device 200 to communicate with one or more other computing devices. Such communication can occur via Input/Output (I/O) interfaces 222. Still yet, device 200 can communicate with one or more networks such as a local area network (LAN), a general wide area network (WAN), and/or a public network (e.g., the Internet) via network adapter 220. As depicted, network adapter 220 communicates with the other components of computing device 200 via bus 218. It should be understood that although not shown, other hardware and/or software components could be used in conjunction with device 200. Examples, include, but are not limited to: microcode, device drivers, redundant processing units, external disk drive arrays, RAID systems, tape drives, and data archival storage systems, etc.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features. The foregoing description should therefore be considered as merely illustrative of the principles, teachings and exemplary embodiments of this invention, and not in limitation thereof.

It is to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A portable device for collecting a breath portion from a patient for analysis, comprising:
a housing structure including:
an inlet port configured to receive the portion of the patient's breath;
an outlet disposed on a longitudinal axis extending from the inlet port, the outlet including a one-way valve;
at least one sensor operatively coupled to the inlet port configured to detect one or more parameters regarding the portion of the patient's breath;
at least one collection container provided with sorbent material adapted to collect the portion of the patient's breath received in the inlet port and configured to be detachable from the housing structure, the at least one collection container extending vertically into the inlet port to traverse a longitudinal axis of the inlet port extending from the inlet port to the outlet;
at least one pump configured to draw the portion of the patient's breath from the inlet port directly through the at least one collection container and configured to facilitate both passage of the portion of the patient's breath through the at least one collection container and capture of the portion of the patient's breath in the at least one collection container; and
a control system configured to control operation of the at least one sensor and at least one pump and which selectively operates the at least one pump based upon a pressure level of the portion of the patient's breath as detected by the at least one sensor.

2. The device as recited in claim 1, wherein the inlet port includes a mask structure configured to conform to the patient's face.

3. The device as recited in claim 1, wherein the inlet port includes a bacterial filter element.

4. The device as recited in claim 1, wherein the device receives a source of air scrubbed to be free of Volatile Organic Compounds (VOCs).

5. The device as recited in claim 4, wherein the housing structure further includes an air port configured to couple to an external device to provide the source of scrubbed air.

6. The device as recited in claim 1, wherein the at least one sensor includes a sensor device configured to detect and measure Carbon Dioxide ($CO_2$) levels in the portion of the patient's breath.

7. The device as recited in claim 1, wherein the at least one sensor includes a sensor device configured to detect and measure the pressure level of the portion of the patient's breath.

8. The device as recited in claim 1, wherein the at least one collection container is cylindrical shaped.

9. The device as recited in claim 1, wherein the control system is configured to operate the at least one pump based upon a Carbon Dioxide ($CO_2$) level of the portion of the patient's breath as detected by the at least one sensor.

10. The device as recited in claim 1, wherein the control system is configured to operate the at least one pump based upon a mathematical function of a Carbon Dioxide ($CO_2$) level, the pressure level, or both the Carbon Dioxide ($CO_2$) level and pressure level of the portion of the patient's breath as detected by the at least one sensor.

11. The device as recited in claim 1, wherein the control system is configured to collect an alveolar, bronchiolar, nasopharyngeal, oropharyngeal, gastro-intestinal, or other portion of the patient's breath or any combination thereof.

12. The device as recited in claim 1, wherein the housing structure includes a computer port configured to couple the control system to an external computing device.

13. The device as recited in claim 12, wherein the external computing device is configured and functional to perform analytics on sensor data captured from the at least one sensor.

14. The device as recited in claim 12, wherein the external device includes a display configured to illustrate operating parameters regarding a selective capture of the portion of the patient's breath.

15. The device as recited in claim 1, wherein the housing structure includes the plurality of sensors, pumps and collection containers.

16. The device as recited in claim 15, configured to capture a first breath sample in the at least one collection container and a second breath sample in one or more different collection containers.

17. The device as recited in claim 16, wherein the first breath sample is different from the second breath sample.

18. The device as recited in claim 1, wherein the inlet port is fluidly coupled to the outlet separate from fluid connection to the at least one collection container.

19. The device as recited in claim 1, wherein the at least one pump has a pressure sensor mounted upstream the at least one pump and downstream the at least one pump.

20. The device as recited in claim 2, wherein the mask structure is a replaceable flexible mask.

21. The device as recited in claim 2, wherein the mask structure has a pressure sensor and the at least one pump has a pump inlet pressure sensor monitorable to detect a poorly fitting mask.

22. The device as recited in claim 8, wherein the at least one collection container is in series with a Lee orifice plate.

\* \* \* \* \*